(12) United States Patent
Skjoedt (10) Patent No.: US 10,179,652 B2
(45) Date of Patent: Jan. 15, 2019

(54) ACTIVE FROST FORECASTING, DETECTION AND WARNING SYSTEM AND METHOD

(71) Applicant: Surewx Inc., Pointe Claire (CA)

(72) Inventor: Klaus Skjoedt, Fredericia (DK)

(73) Assignee: Surewx Inc., Pointe Claire, Quebec ( * ) Notice: Subject to any disclaimer, the term of this patent is extended or adjusted under 35 U.S.C. 154(b) by 223 days.

(21) Appl. No.: 14/908,677

(22) PCT Filed: Jul. 29, 2014

(86) PCT No.: PCT/CA2014/050714
§ 371 (c)(1),
(2) Date: Jan. 29, 2016

(87) PCT Pub. No.: WO2015/013822
PCT Pub. Date: Feb. 5, 2015

(65) Prior Publication Data
US 2016/0176530 A1    Jun. 23, 2016

Related U.S. Application Data

(60) Provisional application No. 61/859,453, filed on Jul. 29, 2013.

(51) Int. Cl.
*B64D 15/20*    (2006.01)
*G01N 25/66*    (2006.01)
(Continued)

(52) U.S. Cl.
CPC ............ *B64D 15/20* (2013.01); *G01N 25/18* (2013.01); *G01N 25/66* (2013.01);
(Continued)

(58) Field of Classification Search
CPC ........ B64D 15/20; B64D 15/22; G01N 25/18; G01N 25/66; G01N 33/0036; G01P 5/00; G01W 1/02; G01W 1/10
See application file for complete search history.

(56) References Cited

U.S. PATENT DOCUMENTS

| 3,422,677 A | 1/1969 | Lockwood |
| 4,222,044 A * | 9/1980 | Boschung ............. G08B 19/02 340/581 |

(Continued)

FOREIGN PATENT DOCUMENTS

| CN | 202676934 | 1/2013 |
| EP | 2615302 | 7/2013 |

OTHER PUBLICATIONS

Manual of Aircraft Ground De-Icing/Anti-Icing Operations (Doc 9640-AN/940) Second Edition—2000, Jan. 1, 2001.

*Primary Examiner* — Lisa Caputo
*Assistant Examiner* — Philip Cotey
(74) *Attorney, Agent, or Firm* — Malloy & Malloy, P.L.

(57) ABSTRACT

An active frost warning system for the forecasting and/or detection of active frost conditions by determining the surface or skin temperature of an active frost sensor and comparing the surface or skin temperature with outside ambient temperature and frost point temperature is provided. The system predicts active frost conditions when the surface or skin temperature of the sensor is less than frost point temperature or when the rate of cooling of the surface or skin temperature indicates that the surface or skin temperature of the sensor will be less than the frost point temperature in the future.

19 Claims, 8 Drawing Sheets

(51) Int. Cl.
  *G01N 25/18* (2006.01)
  *G01N 33/00* (2006.01)
  *G01P 5/00* (2006.01)
  *G01W 1/02* (2006.01)
  *G01W 1/10* (2006.01)

(52) U.S. Cl.
  CPC ............ *G01N 33/0036* (2013.01); *G01P 5/00* (2013.01); *G01W 1/02* (2013.01); *G01W 1/10* (2013.01)

(56) References Cited

U.S. PATENT DOCUMENTS

| | | | | |
|---|---|---|---|---|
| 4,766,369 A * | 8/1988 | Weinstein | ............ | B64D 15/20 244/134 F |
| 5,523,959 A * | 6/1996 | Seegmiller | ............ | B64D 15/20 244/134 F |
| 5,710,408 A * | 1/1998 | Jones | ............ | B64D 15/22 219/213 |
| 5,763,858 A * | 6/1998 | Jones | ............ | B64D 15/22 219/213 |
| 6,157,305 A * | 12/2000 | Lester | ............ | G01W 1/10 340/587 |
| 6,194,685 B1 | 2/2001 | Rutherford | | |
| 6,535,141 B1 * | 3/2003 | Doherty | ............ | A01C 17/00 340/580 |
| 9,110,197 B2 * | 8/2015 | Guffond | ............ | G01W 1/02 |
| 2009/0149997 A1 | 6/2009 | Stothers | | |
| 2010/0004863 A1 * | 1/2010 | Ladow | ............ | G01W 1/02 702/3 |
| 2010/0116940 A1 * | 5/2010 | Picco | ............ | B64D 15/20 244/134 F |
| 2010/0149785 A1 * | 6/2010 | Dubuc | ............ | B60Q 1/0005 362/92 |
| 2012/0099616 A1 * | 4/2012 | Penny | ............ | B64D 15/20 374/16 |
| 2014/0192356 A1 * | 7/2014 | Antikainen | ............ | G01S 17/58 356/342 |

* cited by examiner

ACTIVE FROST FORECASTING, DETECTION AND WARNING SYSTEM AND METHOD

FIELD OF THE INVENTION

The invention pertains to the field of de-icing, and in particular, to an active frost forecasting, detection and warning system and method that provide information to assist aircraft de-icing operations such as a warning or indication of current and/or future conditions conducive to active frost formation.

BACKGROUND OF THE INVENTION

Frost can be undesirable in a number of applications and in particular, in the airline industry where, globally, approximately ⅓ of all aircraft deicing operations are performed to remove frost from critical aircraft surfaces. At some airports, frost removal can account for over 75% of deicing events.

Frost has a significant negative impact on aerodynamics. The height and close spacing of frost crystals over a wing surface can be such that it disturbs the airflow much more severely than other forms of frozen contamination. The aerodynamic effect of frost on lift is most pronounced when frost is located on or near a wing's leading edge, and the lift loss effect is the most severe for aircraft without leading edge devices. Frost's impact on drag is most severe when it is distributed extensively over an aircraft. In this case, the aircraft is unlikely to achieve a predicted climb gradient. Thus, frost affects an aircraft's performance and handling qualities and can prove to be lethal irrespective of the size of the aircraft involved.

Lift can decrease by as much as 30% with an attendant rise in drag by as much as 40%. Airflow disturbance caused by frost can also result in control difficulties, especially if the frost is asymmetrically distributed from wing to wing, such as might be the case if one wing was in the early morning sunlight and the other was in the shade.

Active frost conditions are defined as the environmental conditions required for the formation of frost. Once active frost conditions have ceased (i.e. environmental conditions do not support frost formation), any remaining frost is defined as passive frost. The FAA defines active frost as frost that actively grows in mass and thickness.

Frost occurs when the surface temperature of an object is below the frost point. Frost point is determined by outside air temperature (OAT) and relative humidity (RH). The ideal conditions for frost accretion are the following:

Outside Ambient Temperature: Below 3° C.
Relative Humidity: Above 60%
Wind Speed: Less than 5 km/h
Sky Condition: Clear, or mostly unobstructed Active frost occurs on aircraft surfaces that are at or below 0° C. and at or below dew point with dew point being the temperature at which water vapor will begin to condense. Relative humidity at the dew point is 100%.

Determining the onset and completion of active frost conditions is critical to aircraft operations, as active frost conditions require different strategies for aircraft de/anti-icing and pre-flight servicing of the aircraft. Passive frost can be removed from critical aircraft surfaces without concern for reoccurrence and as such anti-icing fluids may not be required. Depending on outside ambient temperatures, it is possible to remove frost without using freeze point depressant fluids, so called deicing or anti-icing fluids, such as propylene glycol, ethylene glycol or others known in the art. Reducing the use of deicing or anti-icing fluid during passive frost removal may lower costs, eliminate or reduce negative environmental impacts, and may result in quicker turnaround time and/or less aircraft delays In the airline industry, if a flight is departing during active frost conditions, not only does any existing frost have to be removed from critical surfaces, but the pilot must ensure that the fluids applied provide sufficient holdover time (HOT) for the aircraft to depart. In current practice, this requires the use of anti-icing fluids which are expensive, have significant negative environmental impacts and usually result in increased aircraft turn around times.

Within the airline industry, aircraft turnaround time, or the task of getting an aircraft to "wheels up" (safely) is of primary importance as any delays on a single flight could delay the aircraft's subsequent flights for the day and a delay in any flight could result in passengers or cargo missing connecting flights. For this reason, airlines often incur extra costs to reduce the risks of delays in "wheels up" time. With respect to frost conditions, there are no reliable indications for active frost. In the absence of knowledge of whether frost is active or passive, airlines need to make the conservative assumption that the frost is active and to treat it accordingly. At some airports, overnighting aircraft are uniformly coated with anti-icing fluid every night to prevent frost formation.

The Society of Automotive Engineers (SAE) sub-committee AC-9C defines frost as "ice crystals formed on a surface by water vapour deposition from the atmosphere." Transport Canada expands on this, describing frost as "a thin white deposit of frozen precipitation which is of fine crystalline texture, that adheres to exposed surfaces usually during below freezing, calm winds, cloudless nights with air of high relative humidity and with no precipitation falling. Often the frost deposit is thin enough for surface features underneath, such as paint lines, to be distinguishable."

Frost forms by deposition of water vapour onto a surface directly from vapour to solid without passing through the liquid stage. Deposition occurs when a surface's temperature falls below the frost point of the air above it. The surface can be cooled to below the frost point in several ways including cold soaking the wing or radiation cooling. The formation of frost does not require 100% relative humidity. In fact, Transport Canada tests suggest that the most rapid frost formation occurs near 75% relative humidity. Testing sponsored by Transport Canada has further revealed that the upper surface of a wing can be as much as 8° C. colder than the ambient air temperature due to radiation cooling at night. Operational crews need to be aware that these conditions are conducive to the formation of frost. The lower the outside air temperature, the more tenaciously the frost appears to adhere to the surfaces.

The frost point (also referred to as 'icing temperature' in some material) is similar to the dew point, in that it is the temperature to which a given parcel of humid air must be cooled, at constant barometric pressure, for water vapor to be deposited on a surface as ice without going through the liquid phase. The frost point for a given parcel of air is always higher than the dew point, at temperatures below 0° C., as the stronger bonding between water molecules on the surface of ice requires higher temperature to break.

Currently no standardized technology or manual approach is being used in aircraft operations to determine active frost conditions. Typically forecast weather conditions are monitored for an indication of whether or not frost formation is likely and the resulting probability is used in planning processes. However, once frost is discovered, usually through visual inspections of aircraft surfaces, there are no methods to reliably determine whether it is active frost (i.e. conditions for continued frost formation persist).

The invention will be used to tell flight crews, airport operators, regulators, other meteorological agencies and other stakeholders about whether or not active frost conditions are present at airport sites.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide an active frost forecasting, detection and warning system and method. In accordance with an aspect of the present invention, there is provided an active frost sensor comprising an upper skin and one or more temperature sensors fixed to the skin. In accordance with some embodiments of the invention, the skin of the active frost sensor is manufactured from a material with good heat transfer properties and/or is insulated on its lower surface. Optionally, the skin can be manufactured from a variety of materials including materials typically used as the skin of commercial aircraft.

In accordance with another aspect of the invention, there is provided an active frost sensor comprising an upper skin manufactured from a material with good heat transfer properties; the skin being insulated on a lower surface of the skin; one or more temperature sensors fixed to the skin; and a means of supplying heat to the skin.

In accordance with another aspect of the invention, there is provided a system for active frost detection comprising one or more active frost sensors comprising an upper skin; and one or more temperature sensors fixed to the skin for measuring skin temperature; one or more sensors for measuring outside ambient temperature; and a means for comparing skin temperature with outside ambient temperature; wherein if the skin temperature is less than outside ambient temperature, the system will provide a warning to indicate that conditions for active frost may be present and/or if the skin temperature is less than the frost point, the system will provide a warning to indicate that conditions for active frost are present. Optionally, the system is further configured to forecast or predict future active frost conditions and in some embodiments, provide a warning when future active frost conditions are likely.

In some embodiments of the invention, the system includes a frost sensor which detects active frost conditions by measuring the surface temperature of an exposed plate with an insulated backing.

In some embodiments of the invention, the system includes the above frost sensor, temperature sensors to measure the outside ambient temperature (OAT), various types of sensors to measure relative humidity, a communication system to collect data from the sensors, a processing system, and a communication system to connect to various interfaces.

In one embodiment, the frost detection and warning system provides three output signals after using sensor inputs to calculate the frost point (or ice point or ice temperature) according to established methods:

(i) If the surface temperature of the frost sensor is greater than OAT, the system will indicate that conditions for active frost are not present.

(ii) If the surface temperature of the frost sensor is less than OAT, the system will provide a warning to indicate that conditions for active frost may be present.

(iii) If the surface temperature of the frost sensor is less than the frost point, the system will provide a warning to indicate that conditions for active frost are present.

In accordance with another aspect of the present invention, there is provided a method for detecting active frost conditions, the method comprising the steps of determining the surface temperature of an active frost sensor; the active frost sensor comprising an upper skin manufactured from a material with good heat transfer properties; comparing the surface temperature with outside ambient temperature and frost point temperature; wherein when the surface temperature is greater than the outside ambient temperature active frost conditions are not present and wherein when the surface temperature is less than frost point temperature active frost conditions are present.

In accordance with another aspect of the present invention, there is provided a method for forecasting active frost conditions, the method comprising the steps of determining the surface temperature of an active frost sensor; the active frost sensor comprising an upper skin manufactured from a material with good heat transfer properties; determining the rate of cooling of the skin of the active frost sensor; comparing the surface temperature with outside ambient temperature and frost point temperature; wherein when the surface temperature is greater than the outside ambient temperature active frost conditions are not present and wherein when the surface temperature is less than frost point temperature active frost conditions are present.

In accordance, with some embodiments the method of forecasting active frost conditions comprises the step of predicting a time in the future when the skin temperature will be at or below the frost point from the rate of cooling of the skin and optionally providing a warning to indicate that active frost conditions are approaching and optionally forecasting a time in the future when they are expected to occur.

BRIEF DESCRIPTION OF THE DRAWINGS

These and other features of the invention will become more apparent in the following detailed description in which reference is made to the appended Figures.

DETAILED DESCRIPTION OF THE INVENTION

Overview of the System:

The active frost warning system provides for the forecasting and/or detection of active frost conditions by determining the surface or skin temperature of an active frost sensor and comparing the surface or skin temperature with outside ambient temperature and frost point temperature. Active frost conditions are predicted when the surface or skin temperature is less than frost point temperature or rate of cooling of the skin indicates that the surface or skin temperature will be less than frost point temperature in the future.

This invention provides an apparatus for use in detecting active frost conditions and a system comprising the same. The system for detecting active frost conditions comprises one or more modules, components, apparatus or sensors, which optionally can be linked to third party systems and/or receive data from third parties, including for example meteorological data. The design of the system can be such that individual modules, components, apparatus or sensors can be replaced or components added to the system as requirements change.

Figure 1:
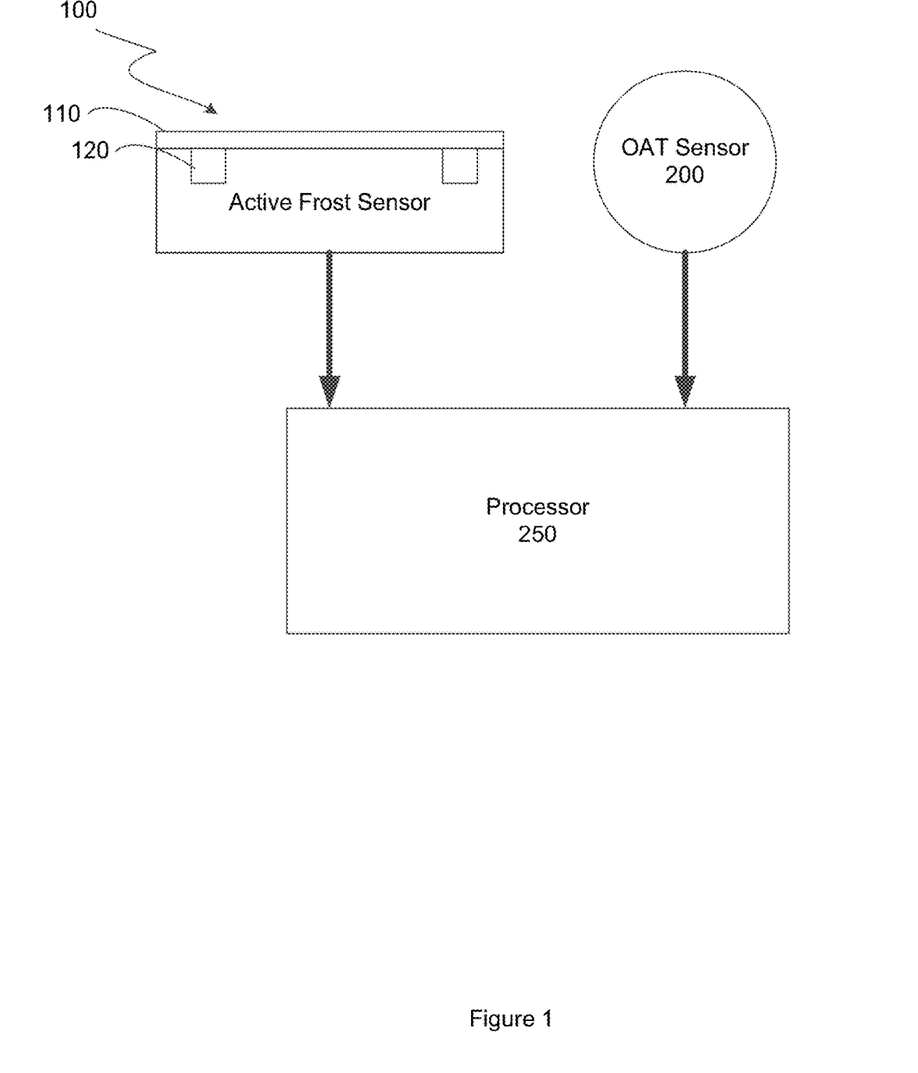
FIG. 1 is a schematic illustrating one embodiment of the system to detect active frost conditions including an active frost sensor, an outside ambient temperature sensor and a processor.

Referring to FIG. 1, the system for detecting active frost conditions comprises one or more active frost sensor 100 comprising a skin 110 and one or more temperature sensors 120 for measuring the temperature at or proximity to the skin, one or more sensors for measuring outside ambient temperature 200 and a processor 250 configured to compare skin temperature with outside ambient temperature. Optionally, the system comprises and/or is operatively associated with an alarm/warning system configured to issue a warning when the outside ambient temperature is below a set point where frost may occur and if the surface temperature of the surface of the frost sensor is less than OAT. The alarm/warning system is optionally configured to issue regular updates on conditions.

In some embodiments, the system comprises a user interface. Optionally, the system can be interfaced with third party system to provide for input of additional data including satellite images and meteorological damage. The system may be configured to receive and transmit data, information, warning or the like to remote locations.

The system may further comprise additional sensors for assessing weather conditions. The additional sensors include means for measuring dew point, such as those commercially available from many manufacturers (e.g. Rotronic, Beko and Vaisala), means for measuring wind speed and/or wind direction; a means for estimating cloud cover such as one or more solar radiation sensors; and one or more ground-based all-sky cameras.

Figure 2:
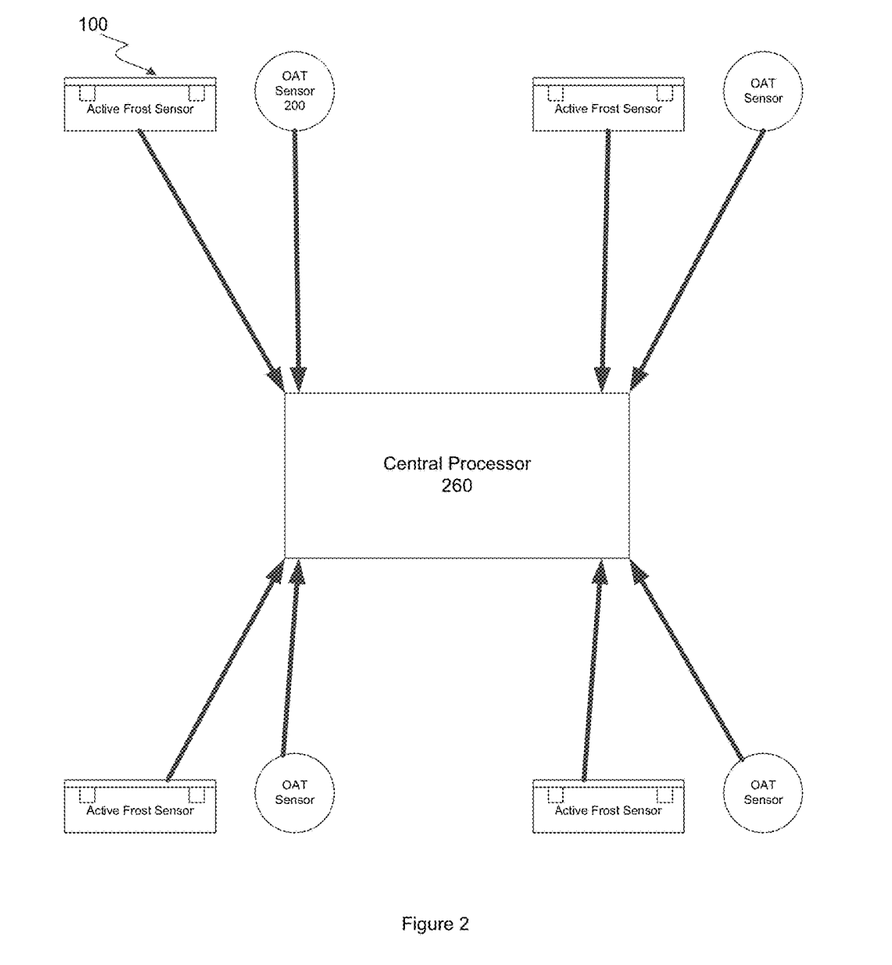
FIG. 2 is a schematic illustrating one embodiment of the system to detect active frost conditions at multiple locations.
Figure 3:
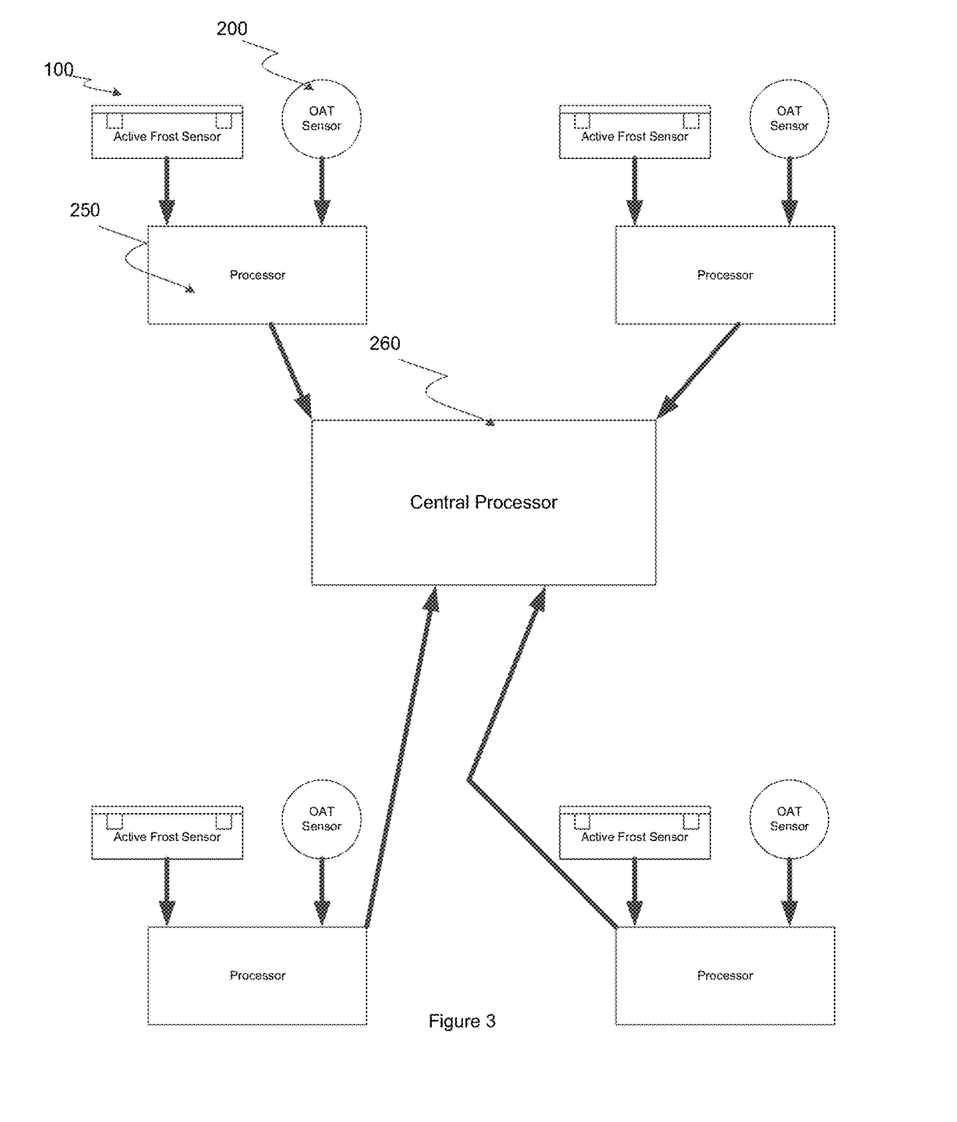
FIG. 3 is a schematic illustrating an alternative embodiment of the system to detect active frost conditions at multiple locations.

In some embodiments, the system is configured to assess active frost conditions at multiple locations. Referring to FIGS. 2 and 3, in such embodiments, one or more active frost sensor 100 and one or more outside ambient temperature sensor 200 are placed at locations in which active frost conditions are to be assessed, such locations, for example, at large airports are individual terminals or gate areas. Optionally, data regarding local conditions is relayed or forwarded to a central processor 260. In some embodiments, as illustrated in FIG. 3, a determination of active frost condition status occurs prior to rely to the central processor.

Figure 4:
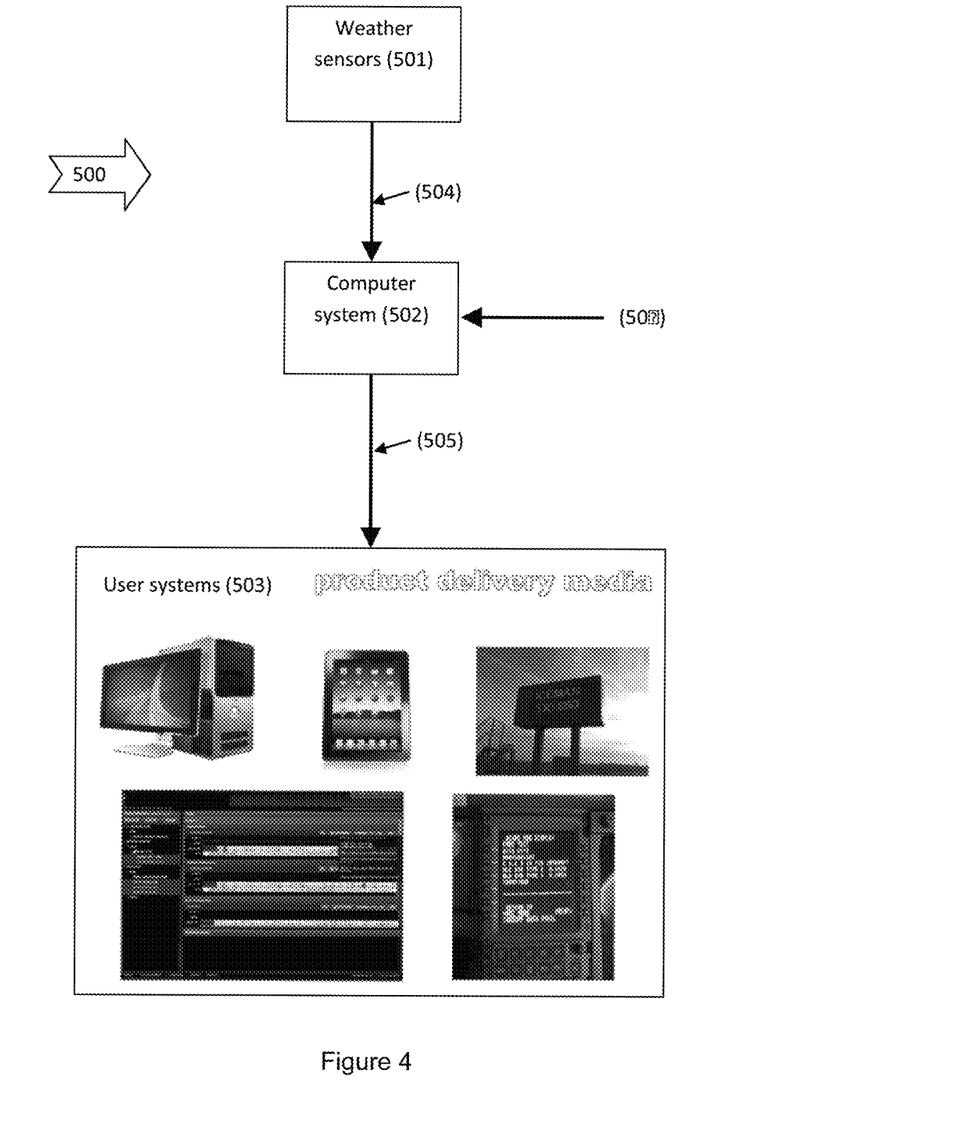
FIG. 4 illustrates an embodiment of the active frost detection and warning system.

The frost detection and warning system may be integrated into a larger system or with other systems. FIG. 4 illustrates an embodiment of the frost detection and warning system that could be used in aircraft de-icing as an example of the invention. The frost warning system 500 includes weather sensors 501, computer system 502, user systems 503, and communication links 504-506. Weather sensors 501 transfer weather data to the computer system 502 over link 504. The computer system 502 transfers information to user systems 503 over link 505. A weather information service, a de-icing information system, a facilities management system or other system (not shown) may also transfer data to the computer system 502 over link 506.

Weather sensors 501 include one or more of the active frost sensor described above and may also include sensors to measure outside ambient temperature, relative humidity, wind speed, dew point, precipitation type, or some other weather measurement. This weather data may also come from other systems over link 506.

Weather sensors 501 may be individual units or may be distributed among multiple components and locations. There could be one or many such sensors. For detection of active frost, multiple sensors could be located to have varying exposure to direct sunlight and this could be factored into the warning system to provide intermediate levels of active frost warning.

As there are advances in commercially available instrumentation, it will be possible to obtain other environmental measurements to indicate active frost conditions and these could be added or substituted for the weather sensors in 501. For example, measurements and calculations to quantify radiation cooling could be weighed against a quantification of convective heat transfer to determine whether active frost conditions are present.

In some embodiments, the system is configured to determine the rate of cooling of a, for example the outer skin of the frost sensor and/or the rate of radiation heat transfer. Optionally, the rate of cooling of the outer skin could be continuously monitored or repeatedly assessed to identify an impending risk of active frost conditions.

In such embodiments, the rate of cooling of the skin is used to predict a time in the future when the skin temperature would approach or drop below the frost point. Optionally, a warning is provided by the system to indicate that active frost conditions are approaching and to forecast a time in the future when they might occur.

The computer system 502 may be any programmed general purpose computer or any special purpose circuitry and equipment as there are many different architectures fit for the purpose. In some examples, the computer system 502 will collect the data, and perform the calculations required to determine whether active frost conditions are present and will generate the data, warnings and information required by the user systems 503.

Communications links 504-506 could use wireless, optical, or some other type of data communication mechanism. Communication links 504-506 could use dedicated links or could be part of a larger communication network. Communication links 504-506 could share some data transfer equipment.

A wide variety of product delivery media could be used in the user systems 503 including personal computers, tablets, smart phones, electronic sign boards, cockpit communications systems, audio systems, etc. The system outputs, such as an active frost warning, can be sent to the flight deck using ACARS or other forms of datalink, via the internet and received using tablets, mobile devices or computers. Information can also be sent to electronic message boards at the deicing positions or at gate locations.

In the context of aircraft de-icing, user systems could be in the de-icing facility, the cockpit, the control tower, airport administration or other location. Levels of warnings could be tailored to specific users and applications. End users could include flight crews, ground de-icing personnel, ground operations personnel, airport administration, airline administration, and tower personnel.

Active Frost Sensor:

The active frost sensor together with measurements of outside ambient temperature provides for the detection of conditions conducive for active frost formation. The active sensor comprises a skin and one or more temperature sensors for measuring temperature of the skin or the temperature proximate to the skin.

The sensor can be a variety of shapes including but not limited to cone shaped, flat, slopped and dome shaped.

In some embodiments the sensor is designed to mimic the structure and/or shape of an object which has an outer or exposed surface which would cool more rapidly than its inner parts or other surfaces; for example, an automobile or other rolling stock, an aircraft or part thereof, an unheated building or enclosure. Optionally, the sensor comprises a frame structure that mimics the ribs and spars of an aircraft wing and, in some embodiments, has a profile similar to that of aircraft wing.

The one or more sensors may be raised above the surface of the ground. In some embodiments, the sensor is at a similar to that of a commercial aircraft wing.

Figure 5:
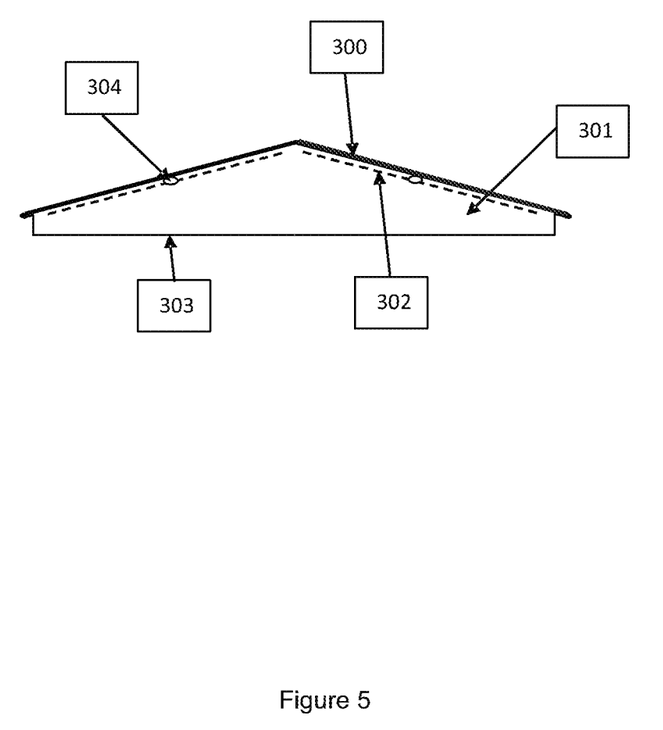
FIG. 5 illustrates an embodiment of an active frost sensor.
Figure 6:
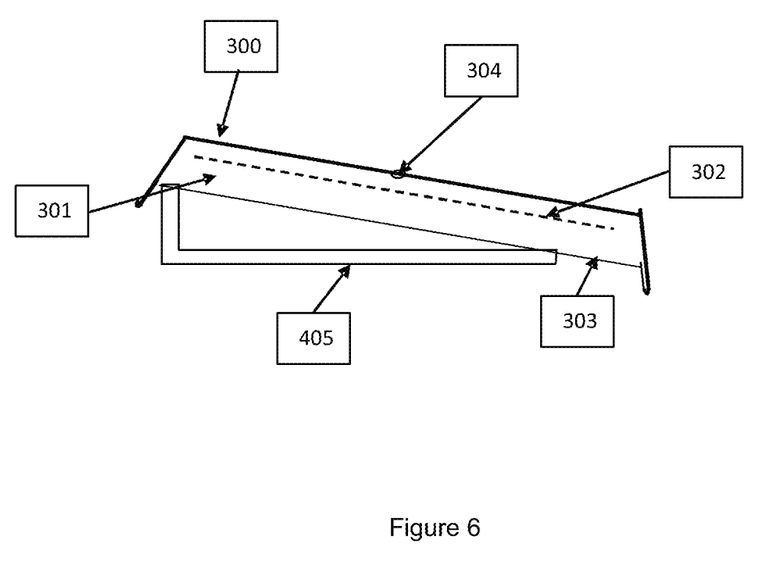
FIG. 6 illustrates an embodiment of an active frost sensor.
Figure 7:
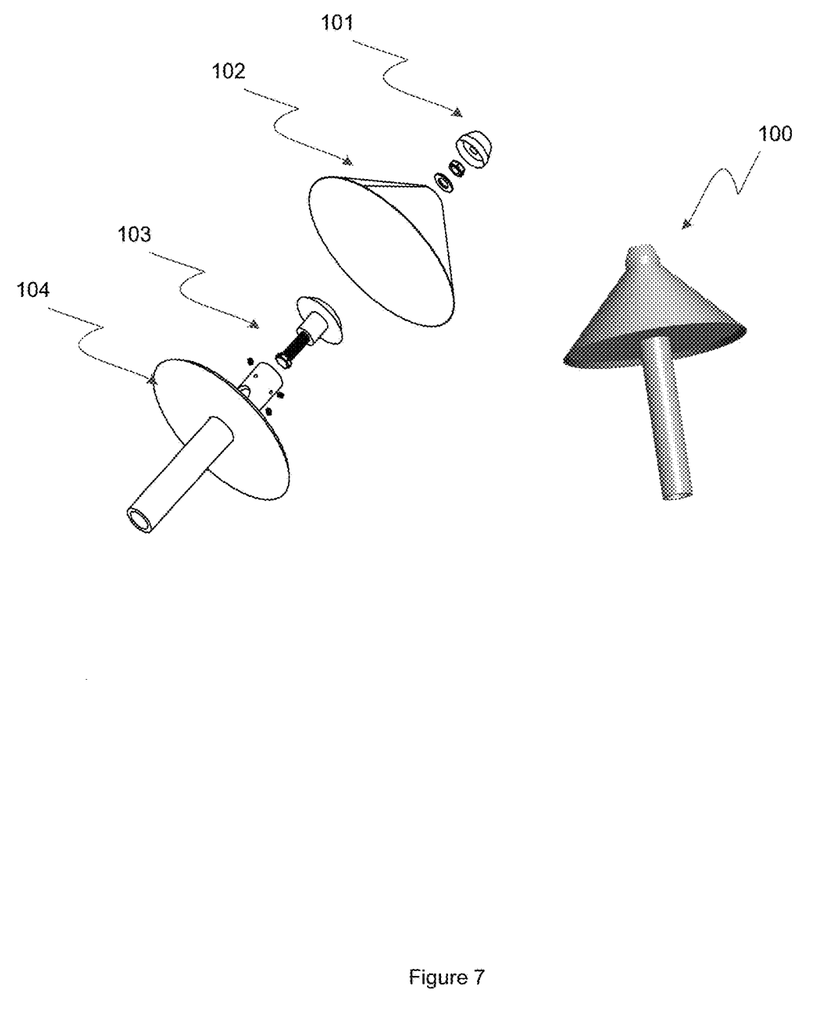
FIG. 7 illustrates an embodiment of an active frost sensor.
Figure 8:
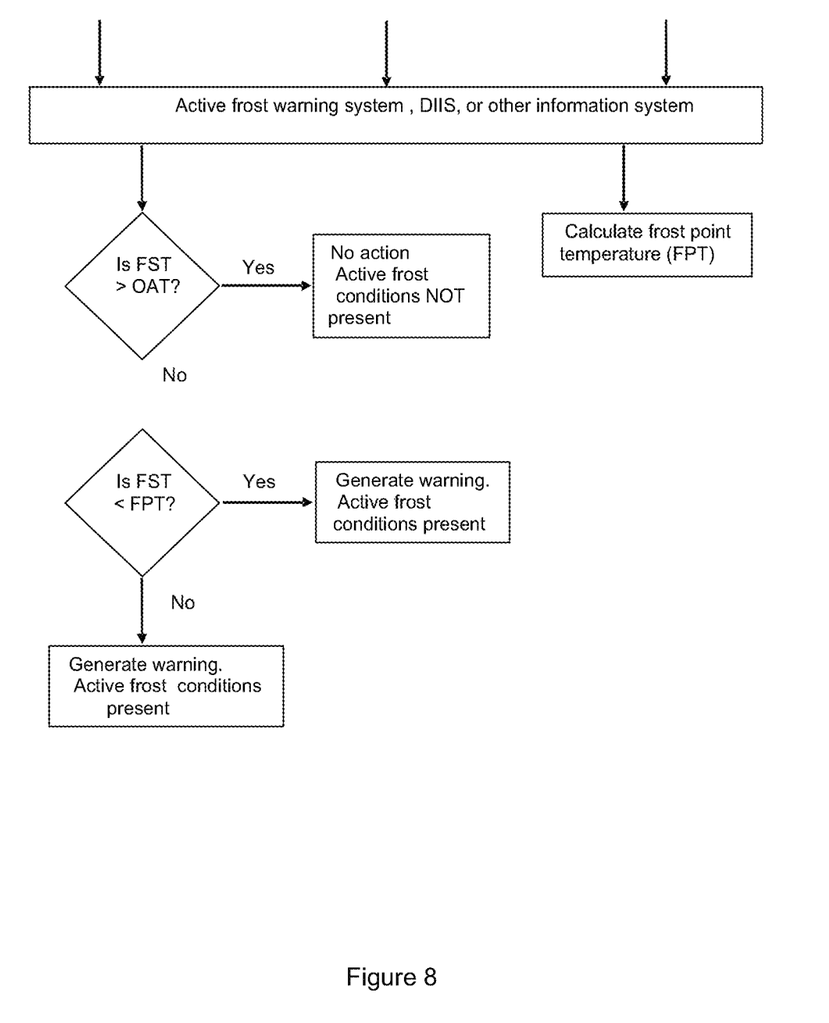
FIG. 8 is a flow chart depicting the steps of one embodiment of the method for detecting conditions conducive for active frost development.

Embodiments of the active frost sensor of the system are shown in FIGS. 5 to 7.

In some embodiments, the sensor is comprised of a flat or curved outside skin 300 which is optionally insulated on one side 301. Temperature sensors 304 are fixed to the skin 300.

Optionally, a heater, or means of supplying heat 302, is installed on the underside of the skin 300. There may be a second skin to enclose the insulation and heater 303, and some means of external support 405. The receiving surface or outside skin of the frost sensor 300 may be made of a painted metal in a variety of shapes. FIGS. 5 and 7 show cone-shaped active frost sensor and FIG. 6 shows a flat, sloped surface. The outside surface is optionally sloped to shed precipitation to ensure a clean surface in frost conditions. In such embodiments, the slope is sufficient to shed accumulated frozen precipitation from all surfaces when the frozen precipitation is melted by the heater 302, and sufficient to shed liquid precipitation from all surfaces so that it doesn't freeze when ambient temperatures drop. The surface may be painted white to maximize radiative cooling. The skin 300 may be made of aluminum, titanium or other metal or material with good heat transfer properties or composite material or alloys.

In some embodiments, the outside skin 300 is insulated on one side 301. The insulation limits heat transfer to the material used to create surface 300. In such embodiments, the insulation is designed to withstand ambient temperatures and weather conditions at the site the sensor is located. The insulation must also be sufficient to prevent heat transfer (e.g. from ambient air) on the back, insulated, side of the skin that might offset heat losses due to radiative cooling.

The amount of insulation required will depend on the heat transfer characteristics of the sensor body which will depend on the material used, the shape and overall size, and the location. The insulation must however be sufficient so that potential (convective) heat gain from ambient air is inconsequential with respect to measurement of the potential radiant heat losses.

In some embodiments, a heater, or means of supplying heat 302, is installed under the outside skin 300. The heater 302 may be an electric blanket or other heat source sized to raise and hold the temperature of the outer skin 300 above 0° C. in the range of winter conditions and quantities of accumulated frozen precipitation expected at the site the sensor is located. The heater 302 allows the skin 300 to be warmed to eliminate any frost or (frozen) precipitation that accumulates on the sensor.

After every precipitation event or prior to any anticipated frost event, the heater 302 will be required to operate to ensure that the outer skin 300 is clean and dry. This can be accomplished with a simple timing cycle which operates the heater at prescribed intervals or can be driven by logic from the computer system 502 in FIG. 4 and inputs from various weather sensors 501 in FIG. 4.

The frost sensor has one or more temperature probes 304 attached to the underside of the outside skin 300. The temperature probe can be a thermistor, thermocouple, or other device suitable for accurate measurement of temperatures around 0° C. and designed to withstand ambient temperatures and weather conditions at the site the sensor is located. The temperature probe 304 could also be attached to the outside surface of 300 or embedded into the material.

Referring to FIG. 7, in one embodiment the active frost sensor 100 comprises frost cap 101, frost cone 102, internal components 103, and frost base 104. The temperature sensors (not shown) are fixed to the underside of the outer skin. Any number of sensors can be fixed to the underside of the outer skin by means known in the art. In one embodiment, four temperature sensors are fixed to the underside of the outer skin 90° apart. The heater (not shown) would also be on the underside of the outer skin. In some embodiments, the heater is a resistance wire.

In some embodiments, the active frost sensor is configured to determine the rate of cooling of its outer skin. Optionally, the rate of cooling of the outer skin is continuously monitored or repeatedly assessed to identify an impending risk of active frost conditions.

In such embodiments, the rate of cooling of the skin is used to predict a time in the future when the skin temperature would approach or drop below the frost point. Optionally, a warning is provided by the system to indicate that active frost conditions are approaching and to forecast a time in the future when they might occur.

The frost detection sensor can be mounted in many different ways. It could be positioned on a pole outside in an area without any horizontal or vertical obstructions or it could be attached to the top of a structure by mean of a bracket, an example of which is shown as 405 in FIG. 6. As previously discussed, as applied to aircraft deicing, multiple sensors could be mounted under slightly different conditions to model the conditions at various gates.

The frost detection sensor measures temperature of the outer skin and compares the measured temperature to another ambient temperature sensing device located nearby, or the ambient temperature provided by a deicing information system (DIIS). If the temperature of the outer skin is less than that measured by the DIIS or the other ambient temperature sensing device, then it can be assumed that radiation cooling is occurring, and therefore the cone surface could be in an active frost condition.

Relative humidity measurements will be obtained from a DIIS or another relative humidity sensing device located nearby. If radiation cooling is occurring, and the relative humidity is high enough (the relative humidity needed to generate frost depends on ambient temperature), then the cone of the frost sensor will begin to accrete frost.

If the surface temperature of the cone is less than the frost point or icing temperature, as calculated by established methods, tables or formulas which depend on the outside ambient temperature and the relative humidity, then a signal or alarm will be generated to warn of the likelihood of active frost conditions.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

I claim:

1. A ground-based system for active frost detection comprising:
    a) at least one active frost sensor comprising an upper skin and one or more temperature sensors for measuring a skin temperature of the skin;
    b) at least one sensor for measuring an outside air temperature, the at least one sensor positioned in an outdoor area with a mounting bracket; and
    c) a processor configured to receive the outside air temperature measurements from the at least one sensor and to determine a frost point from the outside air temperature measurements and relative humidity, the processor further configured to compare the skin temperature with the outside air temperature and the frost point; wherein the system is configured to provide a warning to indicate that conditions for active frost may be present if the processor determines that the skin temperature is less than the outside air temperature and the system is further configured to provide a warning to indicate that conditions for active frost are present if the processor determines that the skin temperature is less than the frost point.

2. The system of claim 1, wherein the skin is insulated on a lower surface of the skin.

3. The system of claim 1, comprising a means of supply heat to the skin of the active frost sensor.

4. The system of claim 1, wherein the skin is manufactured from the skin material of a commercial aircraft wing.

5. The system of claim 4, wherein the active frost sensor comprises a frame structure that mimics ribs and spars of an aircraft wing fragment.

6. The system of claim 5, wherein the skin comprises aluminum or a composite material.

7. The system of claim 6, wherein the composite material comprises aluminum or carbon fibers.

8. The system of claim 1, wherein the one or more temperature sensors are configured to continually measure the temperature of the skin.

9. The system of claim 1, wherein the processor is configured to determine a rate of cooling of the skin.

10. The system of claim 1, wherein the system comprises a means for measuring relative humidity.

11. The system of claim 1, wherein the system comprises one or more means for measuring dew point.

12. The system of claim 1, wherein the system comprises one or more means for measuring wind speed and/or wind direction.

13. The system of claim 1, wherein the system comprises a means for estimating cloud cover.

14. The system of claim 13, wherein the means for estimating cloud cover comprises one or more solar radiation sensors or one or more ground-based all-sky cameras.

15. The system of claim 1, wherein the system comprises distributed sensors.

16. The system of claim 1, wherein the system is further configured to forecast active frost condition.

17. The system of claim 16, wherein the system is configured to determine a rate of radiation heat transfer.

18. The system of claim 16, wherein the rate of radiation heat transfer is determined from the rate of cooling of the skin.

19. The system of claim 18, wherein the rate of cooling of the skin is used to predict a time in the future when the skin temperature would approach the frost point and the system is configured to provide a warning to indicate that active frost conditions are approaching.

* * * * *